United States Patent [19]

Allen et al.

[11] Patent Number: 5,094,959
[45] Date of Patent: Mar. 10, 1992

[54] METHOD AND MATERIAL FOR MEASUREMENT OF OXYGEN CONCENTRATION

[75] Inventors: George Allen, San Diego; Henry K. Hui, Laguna Niguel; Amos Gottlieb, San Francisco, all of Calif.

[73] Assignee: FOxS Labs, Carlsbad, Calif.

[21] Appl. No.: 343,423

[22] Filed: Apr. 26, 1989

[51] Int. Cl.$^5$ .................................. G01N 21/64
[52] U.S. Cl. .................. 436/172; 422/82.07; 422/2.08; 422/86; 436/68; 436/136; 436/138; 436/178
[58] Field of Search .............. 436/68, 136, 138, 167, 436/169, 172, 178; 422/55-58, 61, 82.07, 82.08, 83, 86, 87, 91; 128/633, 634; 250/459.1, 483.1

[56] References Cited

U.S. PATENT DOCUMENTS

| Re. 31,879 | 5/1985 | Lubbers et al. | 436/133 |
|---|---|---|---|
| 3,612,866 | 10/1971 | Stevens | 250/71 |
| 4,075,493 | 2/1978 | Wickersheim | 250/461 R |
| 4,255,053 | 3/1981 | Lubbers et al. | 356/318 |
| 4,399,099 | 8/1983 | Buckles | 422/58 |
| 4,476,870 | 10/1984 | Peterson et al. | 128/634 |
| 4,548,907 | 10/1985 | Seitz et al. | 422/82.07 X |
| 4,833,091 | 5/1989 | Leader et al. | 436/68 X |
| 4,849,172 | 7/1987 | Yafuso et al. | 436/138 X |
| 4,968,632 | 11/1990 | Brauer et al. | 436/136 |

FOREIGN PATENT DOCUMENTS 106086 5/1974 German Democratic Rep. .

OTHER PUBLICATIONS

Seitz, et al., "Luminescence Ratio Indicators for Oxygen", Anal. Chem., vol. 59, pp. 279-283, 1987.

Primary Examiner—Robert J. Hill, Jr.
Attorney, Agent, or Firm—Fulwider, Patton, Lee & Utecht

[57] ABSTRACT

The analyte sensing system utilizes a sensor indicator which may be a perlyene derivative, coronene, or naphtho [8,1,2-abc] coronene in an analyte permeable silicone matrix. The matrix is irradiated with light of a specific wavelength, and fluorescence emissions of the dye indicator is measured over two different emission spectra having different sensitivities to the analyte. The emission spectrum which is less sensitive to quenching by the analyte can be used as a reference for determining the analyte concentration based upon a ratio of the intensities of the different emission spectra.

12 Claims, 2 Drawing Sheets

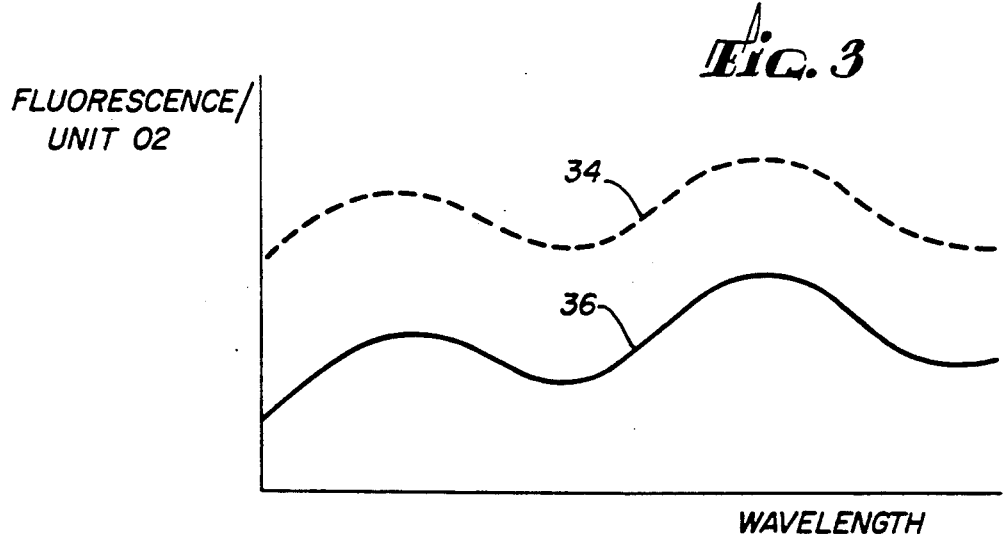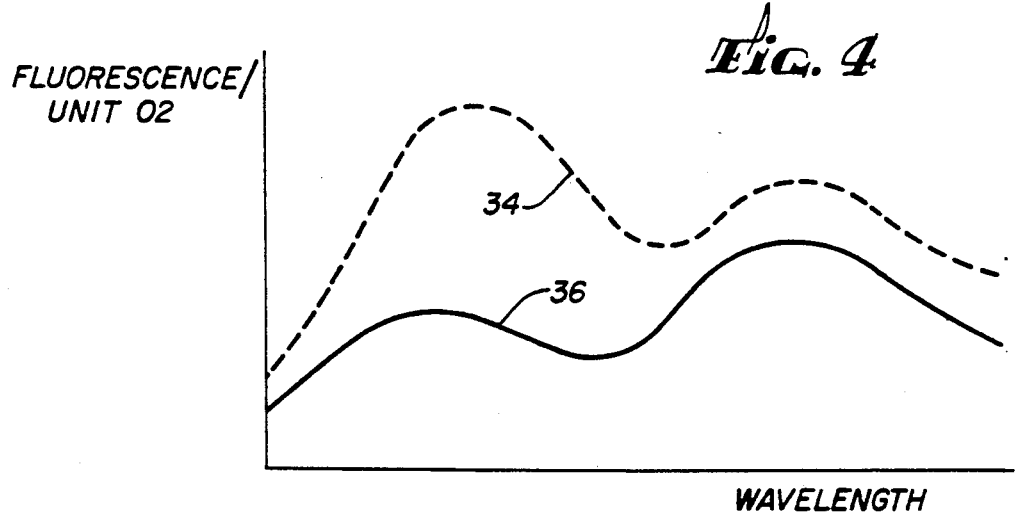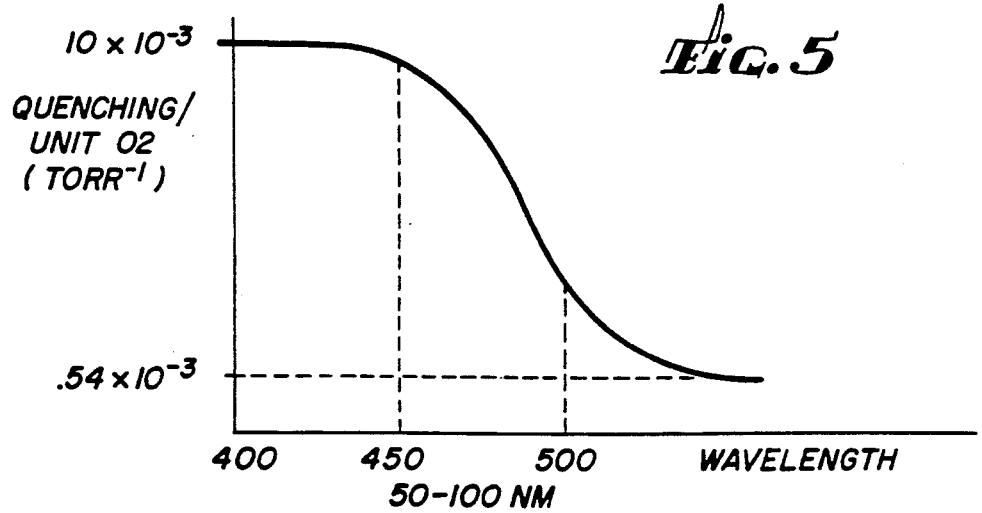

METHOD AND MATERIAL FOR MEASUREMENT OF OXYGEN CONCENTRATION

BACKGROUND OF THE INVENTION

1. Field of the Invention

This invention is generally related to the measurement of concentrations of elements, compounds or other analytes in a fluid or in a gaseous mixture, and more specifically, to the measurement of concentrations of oxygen in a fluid or in a gaseous mixture.

2. Description of the Related Art

A number of methods and apparatus have been developed to measure concentrations of an analyte such as elements or compounds in a fluid or a gaseous mixture. These measurement methods and apparatus have become particularly important in modern medicine, where blood chemistry and other life-critical diagnostic and monitoring measurements have become increasingly important to the sophisticated treatments available. Among such measurement methods and apparatus have been those directed to the measurement of the concentration of oxygen in the blood based upon the phenomenon of quenching of the emissions from certain dyes which are used as indicators. Systems incorporating these methods have been incorporated into intravascular catheters which are used to measure concentrations of oxygen in the blood. In such catheters, optical fibers are used to conduct excitation light generated in an external instrument to the sensing element incorporating the indicator at the distal tip of the catheter and to transmit the resulting emitted light from the sensing element back to the detection system of the external instrument.

While such measurement methods have been shown to be quite useful and have acceptable sensitivity and accuracy, the indicated oxygen concentration often tends to drift or otherwise show inaccuracies or biases, since the intensity of the fluorescence is a function of a number of factors related to the apparatus and dye in addition to the oxygen concentration. These factors include the power of the excitation light, transmission of the optical fiber, the temperature of the sample, the concentration of the indicator dye, and the local environment of the indicator (e.g., changes in the dye-matrix conformation when the dye is immobilized in an analyte permeable matrix). It has been widely recognized that optical sensors show greatly enhanced performance and/or stability when the system includes a means for referencing the intensity of the output to a stable independent source. Ideally, the intensity of this second source should illustrate the same variation in intensity from factors that influence the oxygen sensitive component, with the exception of the oxygen sensitivity. In that case, the quotient of the two fluorescences will yield a ratio which is dependent only upon the concentration of oxygen.

A variety of different approaches have been proposed to provide such reference means, including providing a sample of the indicator which is not exposed to the oxygen, the use of a separate indicator compound or the use of a different chemical form of the indicator. All of these approaches result in a more complex apparatus that may not necessarily provide compensation for a variety of allied indicator degradation phenomena, such as differential photobleaching or differential leaching of the indicator and reference compounds from the sensing element. While it has been suggested that a single chemical compound can be used as both as an indicator and a reference material o the basis of ratioing the fluorescence and phosphorescence of that compound, the reagents developed for such use have not been suitable for the analysis of aqueous and other liquid samples and such a method has been shown to be of limited utility.

There remains, therefore, a need for a means of referencing the output of indicators which employ the phenomenon of fluorescent quenching which is simple and easily implemented in catheter systems and which provides a means of accurate normalization within a wide variation in the fluorescent emission of the indicator. Furthermore, it would be extremely helpful if such a method could be applied to a variety of indicators and does not require additional complex electronics or optics associated with the excitation and measurement scheme.

SUMMARY OF THE INVENTION

The invention provides a method and apparatus by which a single quantity of a species of indicator may be used as both the indicator and the reference element. Certain conventional blood oxygen chemistry sensors utilize as the species incorporated in the indicator a dye which fluoresces when irradiated with light of a certain wavelength. One particular use for such sensors is the measurement of oxygen concentration in the blood. If the dye is exposed to a fluid containing oxygen, the fluorescence will be quenched in proportion to the concentration of oxygen in the fluid. However, calibration of the output of such a method is not simple, and the fluorescence may degrade without any extrinsic indication, thereby causing an undetected error in the measurement.

The present invention uses appropriate indicators, namely polynuclear aromatics, or more specifically, perylene derivatives, together with an appropriate matrix, such as crosslinked polydimethyl siloxane to provide a sensor element for insertion in the blood stream, preferably by means of an appropriate catheter system. By irradiating the resulting matrix with light of a specific wavelength or wavelength range, which may or may not be the wavelength of maximum absorption, while measuring the fluorescent emission over at least two other specific wavelength ranges, different portions of the emission spectrum have been observed to have different sensitivities to oxygen quenching. By choosing certain perylene derivatives, dispersed or immobilized in a silicone matrix, important and unexpected benefits are derived, in that the normalization of emission of the dye can be derived from the emission of the dye itself, rather than from another sample of that dye or a similar one, thereby reducing the complexity of the sensing method and apparatus, and eliminating the uncertainty of measurement of emission of a sample different from that which is making the prime measurement. When the same dye is excited in an organic solvent, the sensitivity to oxygen is nearly the same over the entire emission spectrum and therefore cannot be practically used as a normalization scheme.

Thus, the use of the normalization scheme of the present invention provides a more accurate indication method than previous methods and further results in a far simpler system and apparatus for measurement of the sample containing the analyte. While the invention has proved to be particularly useful for measurement of oxygen samples in the blood by use of a catheter carrying a sensor module incorporating the indicator, the method should also prove advantageous for any measurement system in which an indicator is activated to cause an output, the level of which is altered by the presence of a quantity to be measured.

From the above, it may be seen that the present invention provides a new and useful method for measuring concentrations of an analyte in a fluid by the use of indicators that emit fluorescence when exposed to external radiation such as light. Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 3 is an illustration of the quenching of fluorescence which occurs when typical oxygen sensitive dye in either silicone or a typical organic solvent is irradiated in the presence of oxygen.

FIG. 4 is an illustration of the quenching of fluorescence as a function of frequency when one of the disclosed dyes, dispersed or immobilized in a silicone matrix, is irradiated in the presence of a given concentration of oxygen.

FIG. 5 is an illustration of the quenching of fluorescence as a function of frequency of output for one of the disclosed dyes, indicating how the output may be ratioed to derive the concentration of oxygen in the sample.

DESCRIPTION OF PREFERRED EMBODIMENT

The present invention is embodied in a system and method that allows the use of a single sample of sensor material to perform both measurement of the analyte and normalization of the fluorescent signal for system perturbations, e.g., changes in excitation intensity, changes in fiber transmission, changes in temperature, changes in dye concentration including photodegradation and leaching of the dye.

Sensors which are used to determine the concentration of oxygen in the blood are well known in the art. Among these sensors are systems which utilize a dye which fluoresces when irradiated with light of a certain wavelength. If the dye is also exposed at the same time to concentrations of oxygen, the fluorescence will be quenched in a predictable way in proportion to the concentration of oxygen in the blood. Furthermore, oxygen quenching of the fluorescence of such dyes is generally uniform across the entire emission band.

The conventional means of normalization of such a system for environmental perturbations involves inclusion of a second dye species which is insensitive to oxygen, but which gives an indication of all changes in fluorescent intensity due to all factors other than a change in oxygen concentration. Such systems are susceptible to differential degradation or differential leaching of the dyes with the result that the measurement method becomes unreliable.

The present invention employs the discovery that when certain oxygen indicator dyes are dispersed or immobilized in a silicone matrix, and are irradiated with light at the frequency of maximum absorption or with light at a frequency not at the frequency of maximum absorption, they will emit fluorescence which is frequency sensitive to the quenching phenomena. By measuring the fluorescent emission over at least two specific wavelength ranges which have different sensitivities to oxygen quenching and by ratioing the output at such frequencies, a normalized measurement of fluorescent quenching due to the presence of oxygen may be measured without the need for a second, distinct dye sample. Thus, the system and apparatus of the present invention provides a more accurate ratiometric method in that it normalizes for dye leaching and/or dye photodegradation, whereas the two dye method does not.

Figure 1:
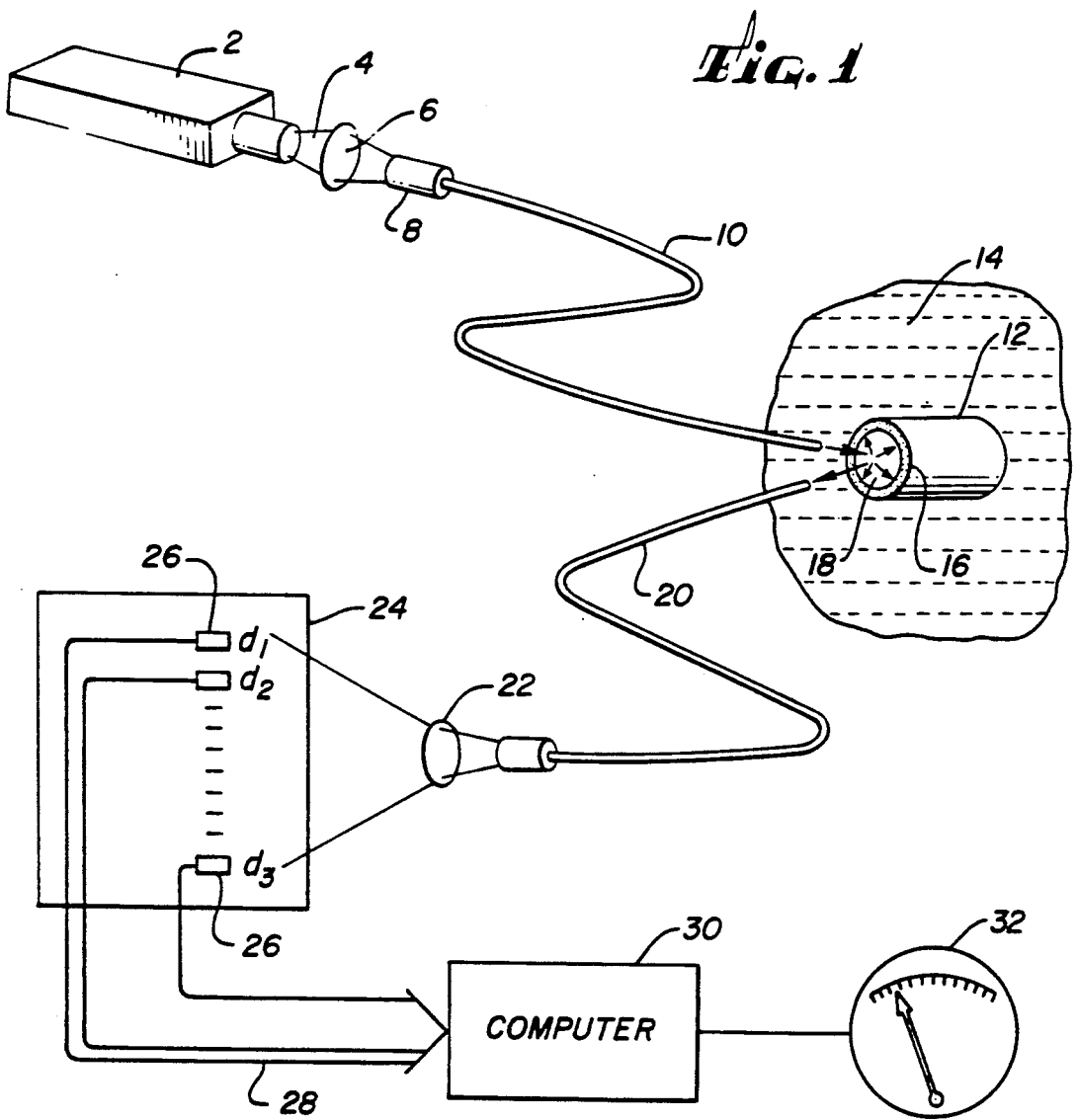
FIG. 1 is a schematic representation of an apparatus according to the present invention, illustrating the relationship between the means of irradiating the sensor and collecting the information for readout of the concentration of oxygen in the sample exposed to the sensor.

FIG. 1 illustrates the general arrangement of the components of an apparatus according to the present invention. A light source 2 provides an output light beam 4 that is focused by a lens system 6 into the connector 8 of an optical fiber 10. Optical fiber 10 conducts the light to a sensor module 12 located in a fluid 14 with a concentration of oxygen to be measured. Sensor module 12 incorporates a portion of dye material (in combination with the matrix to immobilize it) generally indicated 16, surrounding the optical material 18. An output optical fiber 20 carries light from indicator 16 to lens system 22, which focuses the light upon detector array 24, containing two or more detectors 26, each of which is sensitive to various output frequencies to be measured. In practice, the detectors may all be identical, but be fitted with filters which filter all but the frequency to be measured by the detector out of the light reaching the detector. The electrical output of such detectors is fed via a system of cables 28 to a computer 30 which calculates the percentage of analyte present on the basis of the ratio of signals detected by the individual detectors and algorithms in the computer representing the sensitivity of the sensor in those frequency bands to the analyte.

The output of the computer may be provided in the form of a meter 32 or other means to provide a direct indication of the concentration of oxygen in the blood stream. While the above apparatus is illustrated in the form of individual optical fibers for the irradiation and collection of data from the sensor module, those skilled in the art will appreciate that other methods, including time multiplexing and beam splitting, may be used to simplify or alter this apparatus for certain applications.

Figure 2:
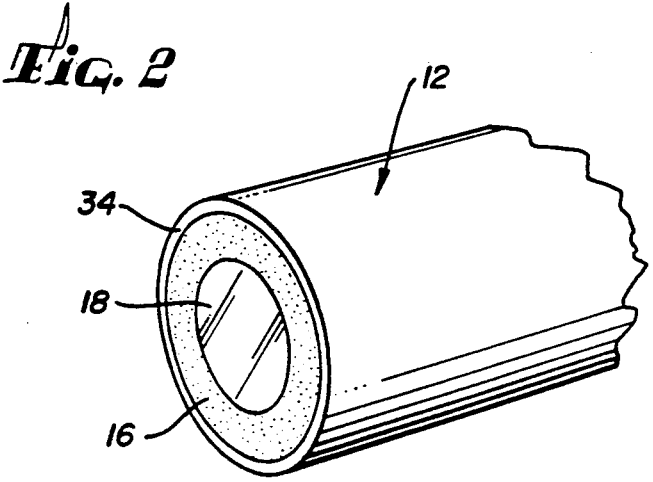
FIG. 2 is an enlarged cross sectional perspective view of the arrangement of the components of the sensor system.

The sensor of the present system is illustrated in more detail in FIG. 2, which shows that the light conductor 18 provides a means of irradiating sensor dye 16 which is immobilized in a matrix surrounding the light conductor. Appropriate systems for such use include the use of indicators such as dyes derived from perylene dispersed in an appropriate matrix such as a crosslinked polydimethyl-siloxane and surrounding the sensor with an oxygen permeable membrane 34 which allows mixing of the oxygen with the dye to promote the quenching by which the measurement of the concentration of the oxygen is performed. Those skilled in the art will appreciate that while a sensor has been illustrated that shows the indicator dispersed around a central light conductor, other systems, such as those in which the light irradiates a capsule of the indicator or a matrix at end of the fiber, are equally adaptable to the invention.

FIG. 3 illustrates that quenching, that is, the difference between the unquenched output level represented by dotted line 34 and the quenched level represented by solid line 36, as a function of oxygen concentration is generally constant over the entire emission band for one of the family of dyes conventionally used for such measurements. Since there are no regions of the spectrum that show differential quenching to oxygen, a ratiometric scheme using a single dye is not possible. This is the normal mode in which sensors according to the prior art operate. For ratiometric operation, an additional dye species must be introduced, thereby adding a region that exhibits a quenching that is different than the oxygen sensing region. Ideally, the second dye will exhibit no quenching, but those exhibiting a small quenching effect are also useable. However, schemes for normalization based on two or more dyes or species will not normalize for loss of dye due to either photodegradation or leaching since the two species may degrade or leach at differential rates. Furthermore, the difference between the two rates may not be constant since each will depend upon environmental conditions such as temperature, oxygen environment, excitation power, analyte medium, etc.

By contrast, FIG. 4 illustrates quenching as a function of oxygen concentration for certain dyes useful for the present invention that are dispersed or immobilized in silicone matrix. In this case, although there is a band at which the indicator is quite sensitive to the presence of oxygen, there will be at least one other band which is relatively insensitive to the concentration of oxygen in the fluid to be measured.

FIG. 5 illustrates the output of such an indicator as a function of frequency per unit of oxygen present as an analyte in a fluid to be evaluated. As can be seen from this illustration, the sensitivity of quenching of the fluorescence varies with the output frequency for a given concentration of oxygen. By ratioing the output of the band that is relatively sensitive, e.g., 400 nm to 450 nm, to one which is relatively insensitive, e.g., 450 nm to 500 nm, a direct indication of the actual concentration of the oxygen may be made. As the dye degrades or leaches from the system the fluorescent intensity of the oxygen-sensitive and the oxygen-insensitive regions of the emission spectrum will change by the same proportion since they result from the same dye species. Therefore, the ratio of the two intensities will remain constant. No drift or inaccuracies will be introduced. For the purpose of this description we define this as an internal ratio scheme, that is, a scheme whereby a single dye species is used as both the indicator and the reference compound. It is necessary that there exists in the emission spectrum at least two regions—one that shows oxygen quenching and one that shows greatly reduced, or more ideally, essentially no oxygen quenching.

The intensity of emission over each of the wavelength ranges is described by the Stern-Volmer expression:

$$Fo/F = 1 + K \times PO2$$

where Fo is the fluorescent intensity in the absence of oxygen; F is the fluorescent intensity at some partial pressure of oxygen, PO2; and, K is the Stern-Volmer constant, which is different substantially for the different emission wavelength ranges (i.e., quenching differs substantially), then the PO2 can be calculated so that the calculated value is independent of factors other than the partial pressure of oxygen. This ratiometric scheme will normalize for the loss of dyes as well as other perturbations.

The following examples are included to assist in further understanding of the invention. It should be understood that these examples are included for the purposes of illustration but are in no way intended to limit the scope of the present invention.

Measurements Using Prior Art Dyes

In order to demonstrate the typical performance of an oxygen sensitive dye, a decacyclene/polydimethylsiloxane matrix was prepared and inserted into the chamber of a fluorescent spectrophotometer. When the sample was irradiated with 395 nm light (the maximum absorbance of the dye), it was observed that the Stern-Volmer K was 0.0035 torr$^{-1}$ across the entire emission spectrum. Furthermore, the Stern-Volmer K was 0.0035 torr$^{-1}$ across the entire emission spectrum when irradiated by light at a frequency not at the maximum absorbency of the dye. Thus, it can be seen that an internal ratio scheme is not possible for this indicator material.

A First Example of Measurements Utilizing The Present Invention

In order to demonstrate the present invention, incorporating the disclosed internal ratio scheme, a coronene/polydimethylsiloxane matrix was prepared and inserted into the chamber of a fluorescent spectrophotometer. When the sample was irradiated with 380 nm light, it was observed that the emission had a wavelength-dependent oxygen sensitivity; the emission at 500 nm had a K value of 0.00054 torr$^{-1}$ while the emission at 420 nm had a K value of 0.010 torr$^{-1}$.

However, when coronene was dissolved in xylene, inserted into the chamber of a fluorescent spectrometer, and irradiated with 380 nm light, it was observed that the emission did not have a wavelength-dependent oxygen sensitivity; the emission had a K value of 0.010 torr$^{-1}$ in the 500 nm region as well as the 420 nm region.

A Second Example of Measurements Utilizing The Present Invention

In order to further demonstrate our invention, a naphtho [8,1,2-abc] coronene/polydimethylsiloxane matrix was prepared and inserted into the chamber of a fluorescent spectrophotometer. When the sample was irradiated with 408 nm light, it was observed that the emission had a wavelength-dependent oxygen sensitivity; the emission at 570 nm had a K value of 0.00044 torr$^{-1}$ while the emission at 480 nm had a K value of 0.0147 torr$^{-1}$.

From the above examples, it is evident that the present invention provides a means of continuously normalizing the output of a fluorescent indicator without the necessity of separate processes or apparatus to perform the ratiometric function. While a particular form of the invention has been illustrated and described, it will also be apparent to those skilled in the art that various modifications may be made without departing from the spirit and scope of the invention. Accordingly, it is not intended that the invention be limited, except as by the appended claims.

We claim:

1. An analyte sensing system which comprises:

a species which displays an output when exposed to external excitation, said output quenched by the presence of an analyte, said species exhibiting a level of said quenching in output varying with the frequency of output, said species being a polynuclear aromatic hydrocarbon based fluorescent dye selected from the group consisting of perylene derivatives;

an analyte permeable silicone matrix in which said species is dispersed or immobilized, said matrix being adapted to be exposed directly or indirectly to a sample containing an analyte to be measured;

a means to excite said species at a first frequency;

a means to measure the output of said species at a plurality of frequencies; and a means to ratio said output in said plurality of frequencies to thereby measure the level of analyte in said sample.

2. The sensing system of claim 1 wherein the analyte permeable silicone matrix in which the species is dispersed or immobilized is crosslinked polydimethylsiloxane.

3. The sensing system of claim 1 wherein the species is coronene.

4. The sensing system of claim 1 wherein the species is naphtho [8,1,2-abc] coronene.

5. A method of sensing the concentration of an analyte in a fluid medium which comprises:

exposing a sample of said fluid medium to an indicator which displays a variation in output as a function of frequency when exposed to an analyte, said indicator being a polynuclear aromatic hydrocarbon based fluorescent dye selected from the group consisting of perylene derivatives and said indicator being dispersed or immobilized in an analyte permeable silicone matrix;

activating said indicator with radiation;

measuring the output of said indicator at a plurality of frequencies; and determining the concentration of said analyte on the basis of the ratio of said plurality of outputs of said indicator.

6. The method of claim 5 wherein the analyte permeable silicone matrix is formed from crosslinked polydimethylsiloxane.

7. The method of claim 5 wherein the indicator is coronene.

8. The method of claim 5 wherein the indicator is naphtho [8,1,2-abc] coronene.

9. An analyte sensing apparatus which comprises:

a species of polynuclear aromatic hydrocarbon based fluorescent dye selected from the group consisting of perylene derivatives, which produces an output when exposed to external excitation, said output varying as a function of the concentration of an analyte exposed to said species, said species further including a variation in output as a function of the frequency of said output when said species is exposed to a given concentration of said analyte;

means to constrain a quantity of said species, said constraining means including an analyte permeable silicone matrix and further providing means to expose at least a portion of said species to said analyte;

means to excite said species;

means to measure the output of said species at a plurality of frequencies of said output; and means to derive the concentration of said analyte from said measurements.

10. The analyte sensing apparatus of claim 9 in which said matrix is crosslinked polydimethylsiloxane.

11. The analyte sensing apparatus of claim 9 wherein the species is coronene.

12. The analyte sensing apparatus of claim 9 wherein the species is naphtho [8,1,2-abc] coronene.

* * * * *

UNITED STATES PATENT AND TRADEMARK OFFICE
CERTIFICATE OF CORRECTION

PATENT NO. : 5,094,959
DATED : March 10, 1992
INVENTOR(S) : George Allen Divers III; Henry K. Hui and Amos Gottlieb It is certified that error appears in the above-identified patent and that said Letters Patent is hereby corrected as shown below:

On title page, item [19] "Allen et al." should read --Divers III, et al.--

Item [75] "George Allen" should read --George Allen Divers III--

Column 2, line 1, delete second "as"

Column 2, line 2, delete "o" and insert --on--

Column 2, line 39, delete "polydimethyl siloxane" and insert therefor --polydimethylsiloxane--

Column 4, line 59, delete "methyl-siloxane" and insert therefor --methylsiloxane--

Signed and Sealed this

Fourteenth Day of June, 1994

Attest:

BRUCE LEHMAN

*Attesting Officer*  *Commissioner of Patents and Trademarks*